US010913066B2

United States Patent
Giri et al.

(10) Patent No.: US 10,913,066 B2
(45) Date of Patent: Feb. 9, 2021

(54) DIAGNOSTIC CHIP

(71) Applicant: Hewlett-Packard Development Company, L.P., Houston, TX (US)

(72) Inventors: Manish Giri, Corvallis, OR (US); Chantelle Elizabeth Domingue, Corvallis, OR (US); Nicholas Matthew Cooper McGuinness, San Diego, CA (US); Jeremy Sells, Corvallis, OR (US); Sirena Lu, Corvallis, OR (US); Melinda M. Valencia, San Diego, CA (US)

(73) Assignee: Hewlett-Packard Development Company, L.P., Spring, TX (US)

( * ) Notice: Subject to any disclaimer, the term of this patent is extended or adjusted under 35 U.S.C. 154(b) by 311 days.

(21) Appl. No.: 15/546,511

(22) PCT Filed: Jan. 30, 2015

(86) PCT No.: PCT/US2015/013782
§ 371 (c)(1),
(2) Date: Jul. 26, 2017

(87) PCT Pub. No.: WO2016/122598
PCT Pub. Date: Aug. 4, 2016

(65) Prior Publication Data
US 2017/0368549 A1 Dec. 28, 2017

(51) Int. Cl.
*B01L 99/00* (2010.01)
*B01L 3/00* (2006.01)
(Continued)

(52) U.S. Cl.
CPC ....... *B01L 3/502753* (2013.01); *B01L 3/5027* (2013.01); *B01L 3/502715* (2013.01);
(Continued)

(58) Field of Classification Search
None
See application file for complete search history.

(56) References Cited

U.S. PATENT DOCUMENTS 6,326,211 B1 * 12/2001 Anderson ........... B01F 11/0071
422/504
7,332,902 B1    2/2008 Vermeire et al.
(Continued)

FOREIGN PATENT DOCUMENTS

CN    103657748 A    3/2014
EP    0859230    8/1998
(Continued)

OTHER PUBLICATIONS

Bohm et al; A Bi-directional Electrochemically Driven Micro Liquid Dosing System with Integrated Sensowactuator Electrodes; Feb, 27, 2004; http://doc.utwente.nl/16906/1/bi-directional—bohm.pdf.
(Continued)

*Primary Examiner* — Paul S Hyun
(74) *Attorney, Agent, or Firm* — Fabian VanCott

(57) ABSTRACT

A microfluidic diagnostic chip may comprise a microfluidic channel, a functionalizable enzymatic sensor in the microfluidic channel, the functionalizable enzymatic sensor comprising a binding surface to bind with a biomarker in a fluid, and a microfluidic pump to pass the fluid over the binding surface. A microfluidic device may comprise a number of pumps to pump a fluid though the number of microfluidic channels and a number of microfluidic channels comprising at least one sensor to detect a change in a chemical characteristic of the fluid in response to presence of the fluid on the sensor.

7 Claims, 6 Drawing Sheets

(51) Int. Cl.
  *G01N 33/543* (2006.01)
  *G01N 15/06* (2006.01)
  *C12Q 1/6804* (2018.01)
  *C12Q 1/00* (2006.01)
  *G01N 15/00* (2006.01)

(52) U.S. Cl.
  CPC ........... *C12Q 1/005* (2013.01); *C12Q 1/6804* (2013.01); *G01N 15/0656* (2013.01); *G01N 33/5438* (2013.01); *G01N 33/54373* (2013.01); *B01L 3/50273* (2013.01); *B01L 2200/0647* (2013.01); *B01L 2200/0668* (2013.01); *B01L 2200/10* (2013.01); *B01L 2200/141* (2013.01); *B01L 2200/143* (2013.01); *B01L 2300/023* (2013.01); *B01L 2300/024* (2013.01); *B01L 2300/027* (2013.01); *B01L 2300/0636* (2013.01); *B01L 2300/0663* (2013.01); *B01L 2300/088* (2013.01); *B01L 2300/1827* (2013.01); *B01L 2400/046* (2013.01); *G01N 2015/0065* (2013.01); *G01N 2015/0687* (2013.01)

(56) References Cited

U.S. PATENT DOCUMENTS

| | | |
|---|---|---|
| 8,510,056 B2 | 8/2013 | Atashbar et al. |
| 8,614,056 B2 | 12/2013 | Davis et al. |
| 2004/0151962 A1* | 8/2004 | Adams .............. H01M 8/04186 429/443 |
| 2005/0009101 A1 | 1/2005 | Blackburn |
| 2006/0073035 A1* | 4/2006 | Sundararajan ........ F04B 43/043 417/412 |
| 2007/0153284 A1 | 7/2007 | Glazier |
| 2009/0068760 A1 | 3/2009 | Nelson et al. |
| 2009/0291507 A1 | 11/2009 | Clemmens et al. |
| 2010/0066346 A1* | 3/2010 | Zhang ................. B81C 1/00166 324/71.1 |
| 2010/0075340 A1* | 3/2010 | Javanmard ......... B01D 15/3804 435/7.1 |
| 2010/0175821 A1 | 7/2010 | Cho et al. |
| 2011/0312518 A1* | 12/2011 | Davis ............... B01L 3/502761 506/9 |
| 2012/0244604 A1 | 9/2012 | Kornilovich et al. |
| 2014/0066734 A1 | 3/2014 | Zdeblick |
| 2014/0225694 A1 | 8/2014 | Sitti et al. |
| 2015/0124012 A1* | 5/2015 | Hays ......................... B41J 2/07 347/9 |

FOREIGN PATENT DOCUMENTS

| | | |
|---|---|---|
| WO | WO-2014178827 | 11/2014 |
| WO | WO-2015116083 | 8/2015 |

OTHER PUBLICATIONS

Handing Fluids in Microsensors; Nov. 1999; https://str.llnl.gov/str/pdfs/11_99.2.pdf.
Torniainen, et al; "Bubble-Driven Interial Micropump"; Physics of Fluids 24; Dec. 11, 2012; http://dx.doi.org/10.1063/1.4769755.

* cited by examiner

DIAGNOSTIC CHIP

BACKGROUND

Infectious diseases and other medical conditions affect human life on a continual basis. Many developments have been made to detect the presence of pathogens in blood or other bodily fluids in order to diagnose a patient's illness. In some cases, a microfluidic device is used to analyze an analyte.

BRIEF DESCRIPTION OF THE DRAWINGS

The accompanying drawings illustrate various examples of the principles described herein and are a part of the specification. The illustrated examples are given merely for illustration, and do not limit the scope of the claims.

Throughout the drawings, identical reference numbers designate similar, but not necessarily identical, elements.

DETAILED DESCRIPTION

Figure 1:
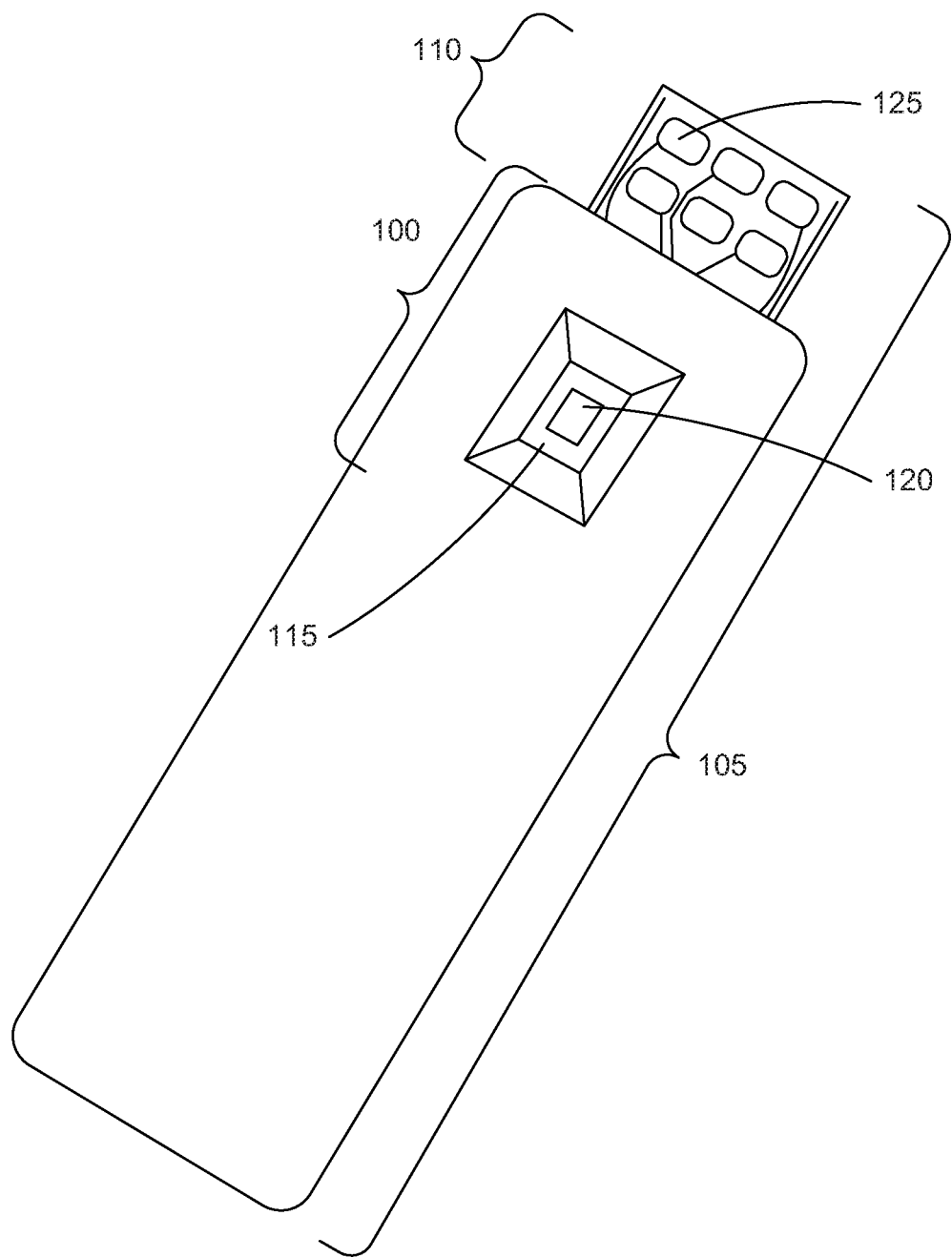
FIG. 1 is a diagram of a microfluidic diagnostic chip incorporated into a cassette for analyzing an analyte according to one example of the principles described herein.

As mentioned above, a microfluidic device may be used to help detect pathogens in the human body and diagnose an illness in a patient. A microfluidic device such as a microfluidic diagnostic chip (MDC) may receive a fluid including an analyte and analyze it for purposes of attempting to diagnose a disease in a patient, immunology analysis, and molecular diagnosis. In some cases, pathogens in the fluid may not be detected readily without further tests conducted in a full lab. The present specification, therefore describes examples including a system and method of detecting pathogens using an MDC as well as continuously monitoring isothermal polymerase chain reactions or polymerase chain reactions conducted under temperature modifications in real time monitoring of both the concentration and molecular weight of deoxyribonucleic acid (DNA) amplification based on impedance signals.

The present application, describes an example microfluidic diagnostic chip which may include a functionalizable enzymatic sensor defined in a microfluidic channel in the microfluidic diagnostic chip. The functionalizable enzymatic sensor may include a binding surface to bind to an analyte (e.g. a biomarker such as an antibody) thereto. For example, fluid may be passed over the functionalizable binding surface via a number of microfluidic pumps to identify the analyte (e.g. biomarker) within the fluid. The identification of the analyte (e.g. biomarker) occurs when the analyte binds to, for example, an antibody on the binding surface. The binding surface may, for example, have a coating.

The present specification further describes an example microfluidic device including a number of microfluidic channels including at least one sensor and a number of pumps to pump a fluid though the number of microfluidic channels wherein presence of the fluid on the sensor detects changes in the chemical characteristics of the fluid.

The present specification also describes an example diagnostic tool for detecting biomarkers and monitoring isothermal polymerase chain reactions in a fluid including at least one microfluidic channel, including a functionalized binding surface with an antibody and a number of impedance sensors wherein the fluid is passed over the functionalized binding surface via a number of microfluidic pumps to identify a biomarker within the fluid, and wherein the number of impedance sensors detect, in real time, changes of the impedance signal indicating isothermal polymerase chain reactions within the fluid.

In the present specification and in the appended claims, the term "fluid" is meant to be understood broadly as any substance that continually deforms (flows) under an applied shear stress. In one example, a fluid includes an analyte. In another example, a fluid includes a reagent or reactant. In another example, a fluid includes an analyte and a reagent or reactant. In still another example, a fluid includes an analyte, a reagent or reactant, among others.

Additionally, in the present specification and in the appended claims the term "analyte" is meant to be understood as any substance within a fluid that may be placed in a microfluidic diagnostic chip (MDC). In one example, the analyte may be any constituent substance within a fluid such as, but not limited to, animal or human blood, animal or human urine, animal or human feces, animal or human mucus, animal or human saliva, yeast, or antigens, among others.

Further, as used in the present specification and in the appended claims, the term "pathogen" is meant to be understood as any substance that can produce a disease. In one example, the pathogen may be found in any fluid as described above.

Still further, in the present specification and in the appended claims the term "reagent" is meant to be understood as a substance or compound that is added to a system in order to bring about a chemical reaction, or added to see if a reaction occurs. A reactant is meant to be understood as a substance that is consumed in the course of a chemical reaction.

Even still further, as used in the present specification and in the appended claims, the term "a number of" or similar language is meant to be understood broadly as any positive number including 1 to infinity.

In the following description, for purposes of explanation, numerous specific details are set forth in order to provide a thorough understanding of the present systems and methods. It will be apparent, however, to one skilled in the art that the present apparatus, systems and methods may be practiced without these specific details. Reference in the specification to "an example" or similar language means that a particular feature, structure, or characteristic described in connection with that example is included as described, but may not be included in other examples.

Turning now to the figures, FIG. 1 is a diagram of a microfluidic diagnostic chip (100) incorporated into a cassette (105) for analyzing an analyte according to one example of the principles described herein. In the example shown in FIG. 1, the MDC (100) is part of the cassette (105). The cassette (105) further includes an electronic device interface (110) electrically coupled to the MDC (100). The interface (110) may allow the MDC (100) to receive instructions and power from an external source such as a computing device. In this example, the MDC (100) is the part of the cassette (105) that receives a fluid including an analyte while the cassette (105) and electronic device interface (110) provide the physical body to house the MDC and the power and logic to operate the MDC respectively.

The cassette (105) may serve as a housing into which the MDC (100) and electronic device interface (110) are housed and protected from contamination and damage. The cassette (105) may also serve as a structure onto which a user may apply pressure in order to connect the electronic device interface (110) to an electronic device, for example directly to a computing device or to a connector that can be attached to a computing device.

The electronic device interface (110) may include any number of electrical contact points (125) that may interface with an input/output port of an electronic device. In one example, the electronic device interface (110) is a universal serial bus (USB) interface capable of electrically coupling to a USB port in an electronic device. In other examples, the electrical contact points (125) of the electronic device interface (110) may fit into a PCI bus, a PCIE bus, a SAS bus, and a SATA bus, among others. In one example, the electronic device interface (110) may include electrical contact points (125) that interlace with a specialized port in a specialized computing device.

The MDC (100) may include a feed tray (115) into which a fluid including an analyte is placed. The feed tray (115) directs the fluid into a fluidic slot (120) of the MDC (100). During operation, the fluid is placed in the feed tray (115) and passed into the fluidic slot (120). When the fluid is in the fluidic slot (120) the MDC (100) receives electrical power from an electrical device via the electronic device interface (110). As will be described below, the MDC (100) may further include an antibody binding surface to be functionalized by an antibody. In one example, the antibody binding surface may be made of gold. In other examples, the antibody binding surface may be made of platinum, tantalum, silicon carbide, or silicon nitride, among others.

The MDC (100) may further include a number of sensors located in a number of microfluidic channels defined in the MDC (100). In one example, the sensors are impedance sensors capable of measuring an impedance value of a fluid including an analyte as the fluid is passed over the sensor. In one example, these sensors may measure the impedance of the fluid over time. In another example, the sensors may measure the impedance of the fluid at any time, for any number of intervals, and over any length of time based on the analysis to be completed. In one example where a microfluidic pump is used to pump the fluid through the MDC (100), the sensors may measure the impedance of the fluid while the pump is not pumping.

Figure 2:
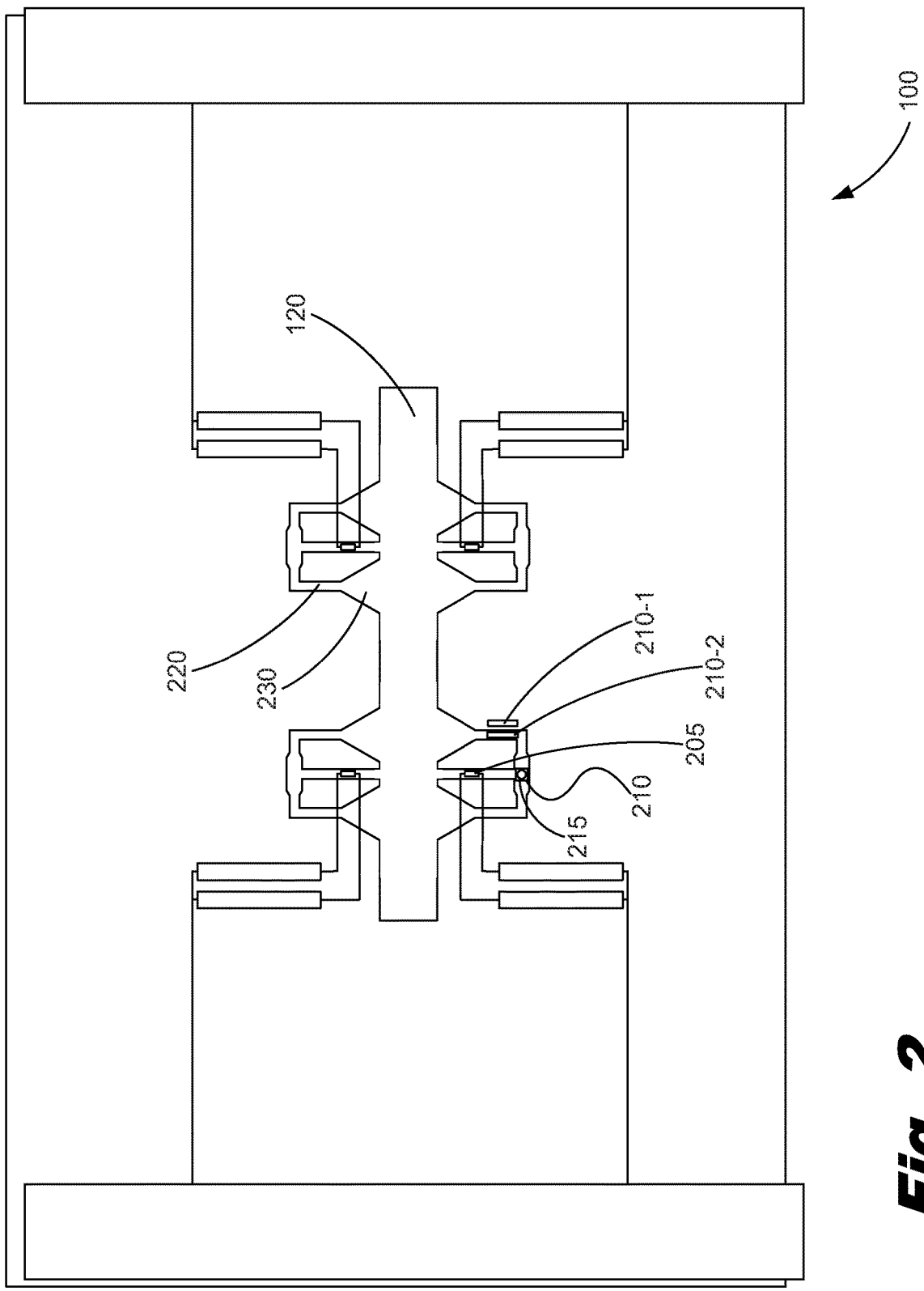
FIG. 2 is a diagram of a microfluidic diagnostic chip according to one example of the principles described herein.

FIG. 2 is a diagram of a microfluidic diagnostic chip (100) according to one example of the principles described herein. The MDC (100) may include a number of sensors (205). Further, the MDC (100) may include a number of resistors (210, 215) that serve as both microfluidic heaters (210-1) and microfluidic pumps (210-2) depending on the amount of voltage applied to the resistor. The MDC (100) may further include a bore (215) that serves as a hole through which an amount of fluid in the MDC (100) is ejected out of a microfluidic channel (120) defined in the MDC (100). During operation of the MDC (100) a number of fluids may be introduced into a fluidic slot (120). The fluid may then flow, via a number of inlets (230), into a number of microfluidic channels (220). The flow of the fluid into these microfluidic channels (220) is initially accomplished via capillary action and subsequently through the use of a resistor (210) as a microfluidic pump (pump resistor). In some examples, the fluid may be mixed, reacted with another fluid, heated, pumped, and recirculated through the fluidic slot (120) and microfluidic channels (220), discharged from the MDC (100), or combinations thereof.

The resistors (210, 215) may be thin film resistors. The thin film resistor may be made of tantalum or tantalum aluminum, platinum, gold, silicon carbide, silicon nitride, tungsten, or combinations thereof. In one example, the thickness of the resistor may be approximately 500 angstroms to 5000 angstroms. The resistor may be encapsulated with a passive film which is then encapsulated with a cavitation film. In one example, the passive film may be made of SiC or SiN and may be approximately 500-2000 angstroms thick. In another example, the cavitation film may be made of tantalum or platinum and may be approximately 500-2000 angstroms thick.

Figure 3A:
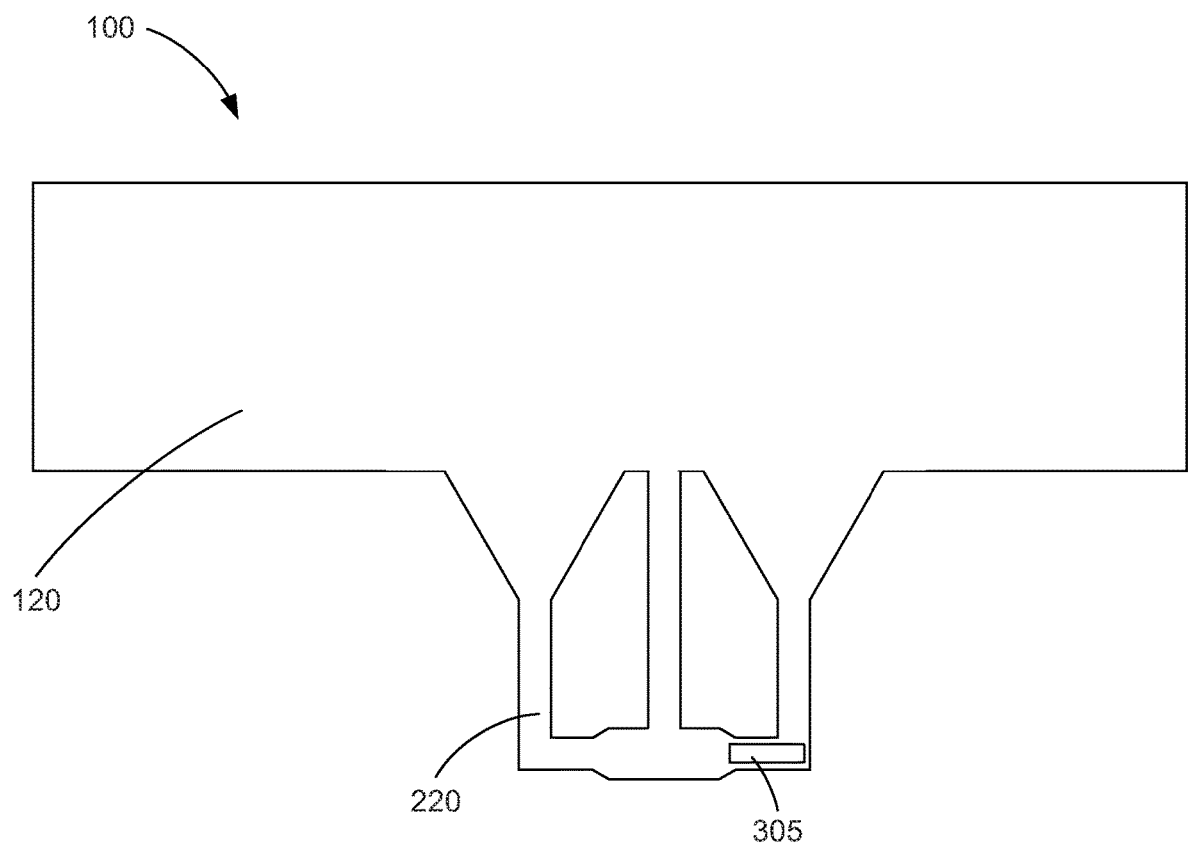
FIGS. 3A and 3B are block diagrams showing a section of a MDC (100) according to two examples of the principles described herein.
Figure 3B:
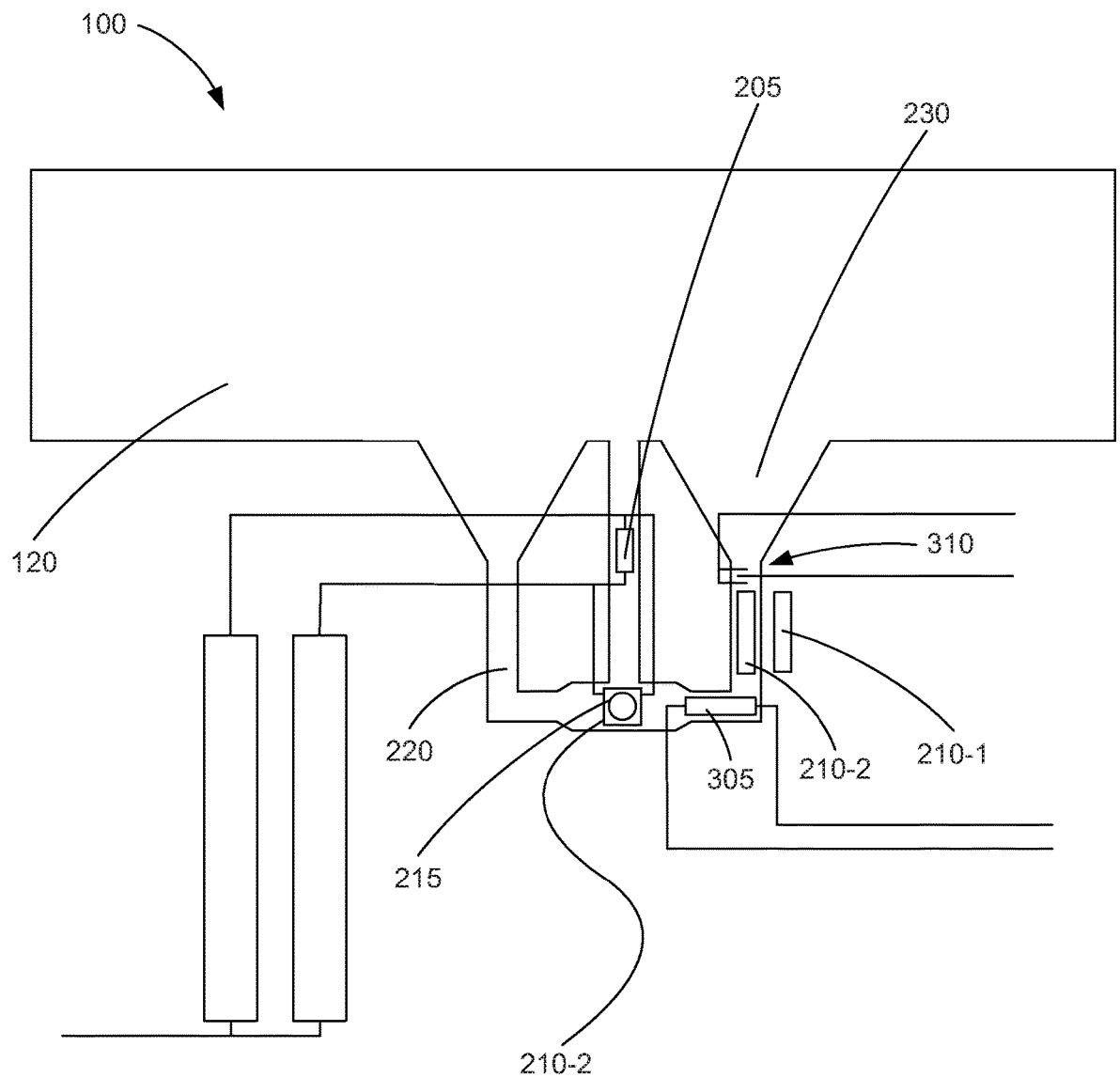

FIG. 3A is a block diagram showing a section of a MDC (100) according to one example of the principles described herein. FIG. 3B is a block diagram showing a section of a MDC (100) according to another example of the principles described herein. The portions shown in FIGS. 3A and 3B include a fluidic slot (120) and a number of microfluidic channels (220) both defined on a silicon substrate defining the MDC (100). The fluidic slot (120) provides a pool from which the fluid may be maintained before entry into the microfluidic channels (220) while the microfluidic channels (220) are the conduits through which the fluid may flow in order to be made to come in contact with the sensors (205) within the microfluidic channels (220). Although FIGS. 3A and 3B shows specifics regarding the placement of the microfluidic channels (220) as well as other components in the MDC (100), the general and specific placement of any given component is meant to be representative of an example of an MDC (100). Consequently, any layout of the individual components in the MDC (100) may be varied and the present specification contemplates the placement of these components in various other layouts without going beyond the scope of the principles described herein.

As mentioned above and shown in FIG. 3B, the resistors (210, 215) may include two types of resistors: a heater resistor (210-1) and/or a pump resistor (210-2). Either kind of resistor (210-1, 201-2) may be placed within any portion of the microfluidic channels (220). In one example, a single resistor (210-1, 201-2) may serve as both a pump (210-1) and a heater (210-2) based on the voltage applied to the resistor (210-1, 201-2). In some examples, a resistor (210-1, 201-2) acts as a heater (210-1) when a voltage less than what results in nucleation of the fluid in intimate contact with the resistor is applied to the resistor. In one example, the voltage applied to the resistor to function as a heater may be less than 5V. In another example, the voltage applied to the resistor to function as a heater may be greater than or less than 5V and may depend further on the properties of the fluid and temperature reached at the interface of the resistor and fluid. In a heater resistor (210-1) the pulse time of the voltage application may vary based on the amount of heat to be created. Here, the longer the pulse and frequency at which the voltage is applied, the more heat is applied by the heater resistor (210-1) while the opposite is also true. In one example, the heater resistor (210-1) has a length of about 5 to 1000 μm and a width of about 5-1000 μm.

In some examples, the resistor (210-1, 201-2) acts as a pump (210-2) when a voltage applied to the resistor (210-2) is approximately 5V or higher. In these examples, the pulse time of the voltage application may be adjusted to vary the size of a drive bubble that is created when the heat from the pump resistor (210-2) is sufficient to vaporize liquid in intimate contact with the resistor (210-2).

The resistor (210-1, 201-2) itself may be made of tantalum, platinum, gold, silicon carbide, silicon nitride, tungsten, or combinations thereof. In the case of a pump resistor (120-2), a rapid Joule heating method (($V^2R$); where V is the voltage, R is the resistance and t is the time) is used to superheat the fluid to create the drive bubble which grows and collapses in less than 10 µs. The rapid bubble creation and collapse causes net flow of fluid within the microfluidic channel (220). In one example, the pump resistor (210-2) has a length of about 5-110 µm and a width of about 5-100 µm. In another example, the pump resistor (210-2) is about 25 µm square.

The MDC (100) shown in FIGS. 3A and 3B may further include an enzymatic sensor (305). The enzymatic sensor (305) may include an electrode made of gold or some other functionalizable material. A functionalized material is any material that can be made functional through the application of a chemical including an antibody onto the surface of the material thereby changing the chemical characteristics of the surface of the material. Some examples may include platinum, tantalum, silicon carbide, and silicon nitride. In one example, the impedance of the gold electrode may be monitored before being functionalized. Then the electrode on the enzymatic sensor (305) may receive across it a chemical including an antibody such that that antibody becomes chemically bonded to the surface of the electrode. The antibody may be delivered in a carrier fluid and to the electrode through the fluidic slot (120) and microfluidic channels (220). The antibody may then be flushed out of the MDC (100) with a wash solution in preparation for a fluid including an analyte such as an antigen to be received in the MDC (100). During this functionalization process, the enzymatic sensor (305) is continually read for changes in the impedance value that quantifies the extent of an antigen or biomarker present in the fluid deposited into the MDC (100).

As will be described in more detail below, the fluid may be passed over the enzymatic sensor (305) causing any antigens within the fluid to chemically bond to the antibodies on the functionalized enzymatic sensor (305). As the antigens chemically bond to the antibodies, the continual monitoring of the impedance values of the enzymatic sensor (305) may be indicated by a change in impedance. This change in impedance is a result of the larger molecule (antibody+antigen) being produced on the surface of the enzymatic sensor (305). The process of producing the antibody/antigen molecule on the surface of the enzymatic sensor (305) may further include recirculating the fluid through the MDC (100) for a predetermined period of time sufficient for the antigens to bond with the antibodies. The recirculation of the fluid may be accomplished by a pump resistor (210-2) pumping the fluid over the resistor at a given rate as described above. Consequently, a diagnosis may be made as to, for example, the concentration of an antigen in a sample of blood thereby allowing a physician to properly diagnose a patient. Other analyses may be conducted including, but not limited to, detection of thyroid specific hormones, prostate specific antigens, the detection of infectious diseases such as H1N1, among others. In one example, analyses may also be conducted on non-human related substances. In this example, the enzymatic sensor (305) may be functionalized with a reagent such that introduction of a sample into the MDC (100) will react with the reagent thereby causing a change in the impedance reading of the enzymatic sensor (305). Consequently, the present specification contemplates the use of the MDC (100) described herein in both a medical and non-medical setting where certain analytes within a fluid may be detected.

In one example shown in FIG. 3B, the MDC (100) may further include a bore (215) to, in cooperation with a pump resistor (210-2) eject an amount of fluid out of the MDC (100). FIG. 3B shows a bore (215) with a pump resistor (210-2) coplanar to each other. During operation, the pump resistor (210-2) may vaporize liquid in intimate contact with it as described above. During the creation of the bubble, an amount of fluid (i.e., analyte, reactant, antigen, etc.) within the microfluidic channel (220) is ejected through the bore (215) and into a fluid reservoir. The fluid reservoir may be a dedicated reservoir in the MDC (100) or in the cassette (105) used to receive an amount of disposed fluid ejected from the bore (215). Using this bore (215) and pump resistor (210-2), the MDC (100) may remove any excess antibody, wash solution, antigen, or other fluid placed in the MDC (100) as described above.

The MDC (100) may further include a heater resistor (210-1) to change the temperature of the fluid in the MDC (100) or change the temperature of the fluid in the MDC (100) for a period of time. In one example, the heater resistor (210-1) may be placed in the microfluidic channel (220). In another example, the heater resistor (210-1) may be placed along the microfluidic channel (220) or another location in the substrate. A temperature sensor (310) may be included in the microfluidic channel (220) to detect the temperature of the substrate on which the MDC (100) is created. The sensed temperature may be presented to a processor in a computing device electrically coupled via the electronic device interface (110) to the MDC (100). Depending on the type of analysis being conducted with the MDC (100), the processor may instruct the computing device to turn up or turn down the heat via the heater resistor (210-1) in order to affect any chemical reaction occurring in the MDC (100). The heater resistor (210-1) and temperature sensor (310) create a thermal sensor feedback loop that creates a thermal controlled and closed loop analysis of the fluid. In this example, a number of, for example, molecular diagnostics may be conducted. In one example, the thermally controlled and closed loop analysis conducted by the thermal sensor feedback loop may be used to detect, analyze, and manipulate DNA within a fluid including an analyte. The use of the heater resistor (210-1) and temperature sensor (310) to conduct a thermally controlled and closed loop analysis may allow a user to detect certain DNA samples from, for example, HIV, H1N1, or any other analysis that is to detect DNA in order to perform an analysis.

In another example, a fluid including a reagent may be introduced into the MDC (100) and allowed to evaporate. The evaporation of the fluid causes the reagent to be left on the surfaces of the microfluidic channels (220), sensors (205, 305), and pumps (210-1, 210-2). Next, a fluid including an analyte may be introduced into the MDC (100) and allowed to react with the reagent already present in the MDC (100). In this example, the reaction may be monitored by the sensors by continually monitoring the impedance value of the fluids before, during, and after the reaction has occurred. This may allow a number of different analyses to be conducted for any number of analytes using the reactant evaporation process described. Additionally, the and temperature sensor (310) and microfluidic heaters (210-1) may be used to monitor and control the temperature during the reaction process where any specific reaction is heat sensitive or heat induced.

Figure 4:
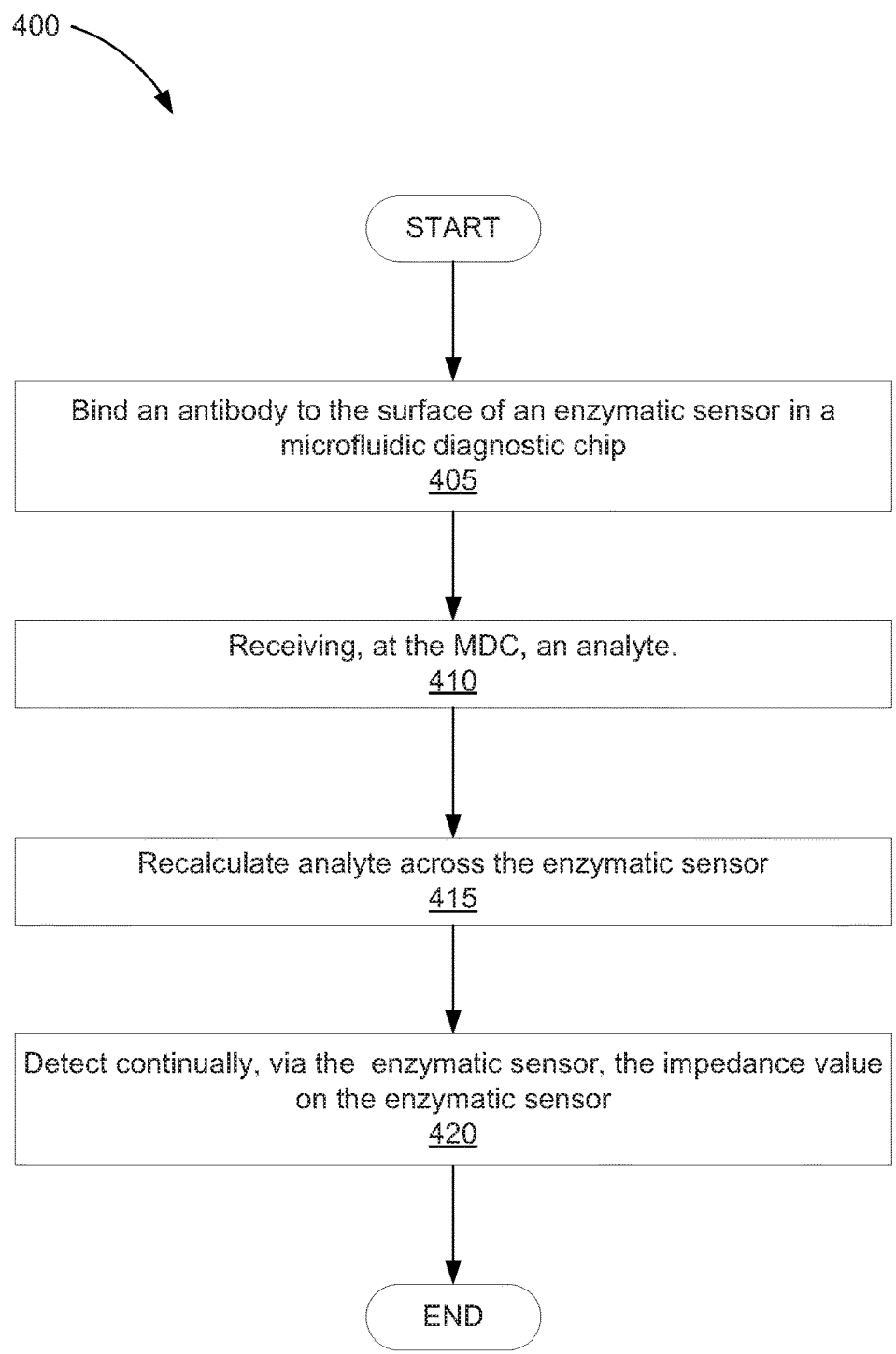
FIG. 4 is a flowchart showing a method of detecting antigens in a fluid according to one example of the principles described herein.

FIG. 4 is a flowchart showing a method (400) of detecting antigens in a fluid according to one example of the principles described herein. The method (400) may start with binding (405) an antibody to the surface of an enzymatic sensor (305) in a MDC (100). As described above, this may be accomplished by introducing a fluid including an antibody into a feed tray (115) of the MDC (100) and pumping the fluid through a microfluidic channel (220) and over the enzymatic sensor (305). During this process, the antibody may bind to the surface of the enzymatic sensor (305).

The method (400) may continue with receiving (410), at the MDC (100), a fluid including an analyte. The fluid may include an antigen therein. The fluid may then be recirculated (415) across or held above the enzymatic sensor (305). During these processes, the impedance value detected (420) via the enzymatic sensor (305) is continually detected. The change in the impedance value is used to detect the presence of an antigen in the fluid as well as help to make a diagnosis.

The method (400) may also be used as a method to conduct a polymerase chain reaction (PCR) in order to amplify a single copy or a few copies of DNA across several orders of magnitude. In this example, the heater resistor (210-1) and temperature sensor (310) are used as a sensor feedback loop to provide the temperature changes and maintenance of a temperature in the MDC (100) to complete the polymerase chain reaction (PCR) process. This method (400) causes the amplification to occur while the fluid in the micro fluidic channels are being recirculated. During the recirculation, an impedance sensor such as the enzymatic sensor (305) constantly monitors the impedance signal such that real-time feedback of the PCR product is obtained.

Figure 5:
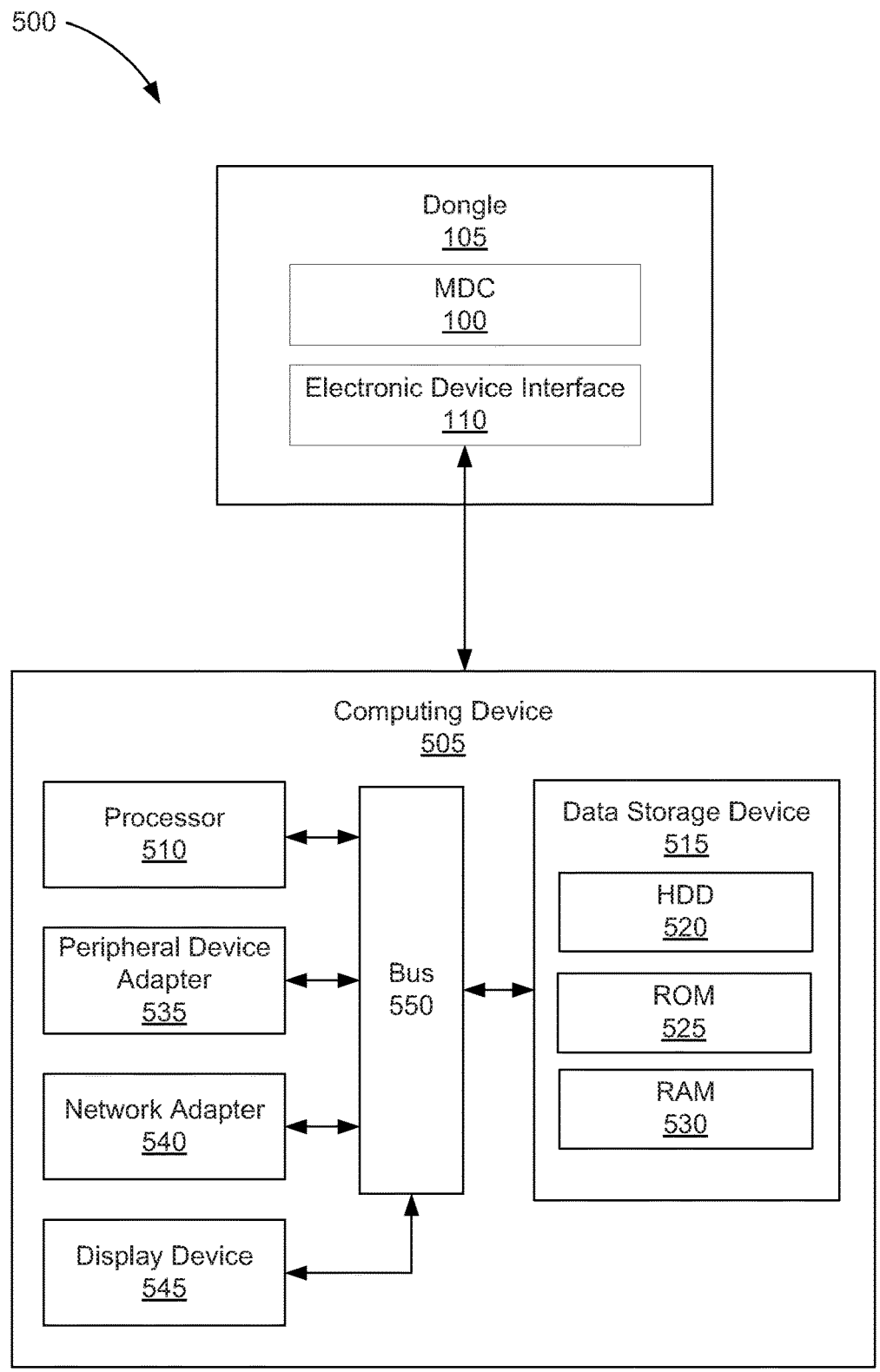
FIG. 5 is a block diagram of a microfluidic diagnostic chip system according to one example of the principles described herein.

FIG. 5 is a block diagram of a microfluidic diagnostic chip system (500) according to one example of the principles described herein. The system (500) includes a computing device (505) and a cassette (105) selectively electrically coupled to the computing device (505). The cassette (105) includes a MDC (100) and an electronic device interface (110) as described above in connection with FIG. 1. In one example, the cassette (105) may be communicatively coupled to the computing device (505) via a USB connector.

The computing device (505) includes various hardware components. Among these hardware components may be a number of processors (510), a number of data storage devices (515), a number of peripheral device adapters (535), and a number of network adapters (540). These hardware components may be interconnected through the use of a number of busses (545) and/or network connections. In one example, the processor (510), data storage device (515), peripheral device adapters (535), and network adapter (540) may be communicatively coupled via a bus (545).

The processor (510) may include the hardware architecture to retrieve executable code from the data storage device (515) and execute the executable code. The executable code may, when executed by the processor (510), cause the processor (510) to implement at least the functionality of receiving a number of electrical signals from the MDC (100) via the electronic device interface (110) and the peripheral device adapter (535), according to the methods of the present specification described herein. In the course of executing code, the processor (510) may receive input from and provide output to a number of the remaining hardware units.

The data storage device (515) may store data such as executable program code that is executed by the processor (510) or other processing device. The data storage device (510) may specifically store computer code representing a number of applications that the processor (510) executes to implement at least the functionality described herein.

The data storage device (515) may include various types of memory modules, including volatile and nonvolatile memory. For example, the data storage device (515) of the present example includes Random Access Memory (RAM) (530), Read Only Memory (ROM) (525), and Hard Disk Drive (HDD) memory (520). Many other types of memory may also be utilized, and the present specification contemplates the use of many varying type(s) of memory in the data storage device (515) as may suit a particular application of the principles described herein. In certain examples, different types of memory in the data storage device (515) may be used for different data storage needs. For example, in certain examples the processor (510) may boot from Read Only Memory (ROM) (525), maintain nonvolatile storage in the Hard Disk Drive (HDD) memory (520), and execute program code stored in Random Access Memory (RAM) (530).

Generally, the data storage device (515) may include a computer readable medium, a computer readable storage medium, or a non-transitory computer readable medium, among others. For example, the data storage device (515) may be, but not limited to, an electronic, magnetic, optical, electromagnetic, infrared, or semiconductor system, apparatus, or device, or any suitable combination of the foregoing. More specific examples of the computer readable storage medium may include, for example, the following: an electrical connection having a number of wires, a portable computer diskette, a hard disk, a random access memory (RAM), a read-only memory (ROM), an erasable programmable read-only memory (EPROM or Flash memory), a portable compact disc read-only memory (CD-ROM), an optical storage device, a magnetic storage device, or any suitable combination of the foregoing. In the context of this document, a computer readable storage medium may be any tangible medium that can contain, or store computer usable program code for use by or in connection with an instruction execution system, apparatus, or device. In another example, a computer readable storage medium may be any non-transitory medium that can contain, or store a program for use by or in connection with an instruction execution system, apparatus, or device.

The hardware adapters (103, 104) in the computing device (505) enable the processor (510) to interface with various other hardware elements, external and internal to the computing device (510). For example, the peripheral device adapters (535) may provide an interface to input/output devices, such as, for example, display device (545), a mouse, or a keyboard. The peripheral device adapters (535) may also provide access to other external devices such as an external storage device, a number of network devices such as, for example, servers, switches, and routers, client devices, other types of computing devices, and combinations thereof.

The display device (545) may be provided to allow a user of the computing device (545) to interact with and implement the functionality of the computing device (545). The peripheral device adapters (535) may also create an interface between the processor (510) and the display device (545), a printer, or other media output devices. The network adapter (540) may provide an interface to other computing devices within, for example, a network, thereby enabling the transmission of data between the computing device (545) and other devices located within the network.

The specification and figures describe a diagnostic chip which may be used to identify a biomarker within the fluid. This diagnostic chip may, for example, allow for detecting an antigen in a fluid on the microfluidic level. On such a scale, the impedance values detected as described above may be more accurate and precise leading to a more accurate diagnosis for a patient. Additionally, the MDC described above may, in some examples, not require an expensive and specially trained technician to operate and a healthcare worker may, in some examples, quickly and easily diagnose a patient without the delay of a lab or the need to be specially trained in the MDC's operation.

The preceding description has been presented to illustrate and describe examples of the principles described. This description is not intended to be exhaustive or to limit these principles to any precise form disclosed. Many modifications and variations are possible in light of the above teaching.

What is claimed is:

1. A microfluidic diagnostic chip, comprising:
    a fluidic slot;
    a microfluidic channel connected at both ends to the fluidic slot;
    a reagent deposited on a surface of the microfluidic channel;
    an impedance sensor in the microfluidic channel, the impedance sensor comprising a binding surface wherein the binding surface functions as an electrode of the impedance sensor;
    a first microfluidic pump in the microfluidic channel to pass fluid over the binding surface;
    a temperature sensor to sense a temperature of fluid in the microfluidic channel;
    a number of nozzles to transfer fluid into a reservoir; and
    a second microfluidic pump to pump fluid through the number of nozzles into the reservoir, wherein the second microfluidic pump is coplanar with a nozzle of the number of nozzles and the second microfluidic pump is concentric with the nozzle of the number of nozzles.

2. The microfluidic diagnostic chip of claim 1, further comprising a number of microfluidic recirculating channels to expose the fluid to the binding surface.

3. The microfluidic diagnostic chip of claim 1, further comprising a thermal sensor feedback loop comprising a heater and the temperature sensor to monitor isothermal polymerase chain reactions within the fluid in real-time.

4. The microfluidic diagnostic chip of claim 1, further comprising the reservoir.

5. A microfluidic device, comprising:
    a number of microfluidic channels comprising at least one impedance sensor to detect a change in a chemical characteristic of a fluid in response to an interaction of the fluid with the impedance sensor, wherein an electrode of the impedance sensor serves as a binding surface functionalized with an antibody;
    a heater in the number of microfluidic channels;
    a temperature sensor to sense fluid temperature near the heater, wherein the temperature sensor is used to control the heater; and
    a number of pumps to pump the fluid through the number of microfluidic channels, wherein a first microfluidic channel of the number of microfluidic channels comprises a channel entrance proximal to a channel exit and wherein the first microfluidic channel forms a loop to recirculate the fluid.

6. The microfluidic device of claim 5, wherein the heater and temperature sensor are part of a thermal sensor feedback loop to monitor isothermal polymerase chain reactions within the fluid in real-time and to continually monitor any change in impedance signal.

7. The microfluidic device of claim 5, wherein the number of pumps each comprises: a thin film resistor: a passive film encapsulating the thin film resistor: and a cavitation film encapsulating the passive film and thin film resistor.

* * * * *